US012584880B2

(12) United States Patent　　(10) Patent No.: US 12,584,880 B2
Tanabe et al.　　(45) Date of Patent: Mar. 24, 2026

(54) GAS SENSOR ELEMENT

(71) Applicant: NGK Insulators, Ltd., Nagoya (JP)

(72) Inventors: Yuma Tanabe, Nagoya (JP); Yuki Kajita, Nagoya (JP)

(73) Assignee: NGK INSULATORS, LTD., Nagoya (JP)

( * ) Notice: Subject to any disclaimer, the term of this patent is extended or adjusted under 35 U.S.C. 154(b) by 368 days.

(21) Appl. No.: 18/187,034

(22) Filed: Mar. 21, 2023

(65) Prior Publication Data

US 2023/0304961 A1　　Sep. 28, 2023

(30) Foreign Application Priority Data

Mar. 24, 2022　　(JP) ................................. 2022-048059

(51) Int. Cl.
　　*G01N 27/406*　　(2006.01)
　　*G01N 27/409*　　(2006.01)
　　*G01N 33/00*　　(2006.01)
(52) U.S. Cl.
　　CPC ..... *G01N 27/4067* (2013.01); *G01N 27/4062* (2013.01); *G01N 27/409* (2013.01); *G01N 33/0037* (2013.01)
(58) Field of Classification Search
　　CPC ........... G01N 27/4067; G01N 27/4062; G01N 27/409; G01N 27/4074; G01N 27/419; G01N 27/4162; G01N 27/30; G01N 33/0037
　　See application file for complete search history.

(56) References Cited

U.S. PATENT DOCUMENTS

| 2008/0121020 A1 | 5/2008 | Oya et al. | |
| 2012/0006099 A1* | 1/2012 | Kajiyama | .......... G01N 27/4071 |
| | | | 73/31.05 |
| 2020/0256270 A1* | 8/2020 | Takeuchi | ........... G01N 27/4065 |

FOREIGN PATENT DOCUMENTS

| JP | 2006319314 A | * 11/2006 |
| JP | 2008046112 A | 2/2008 |
| JP | 2008-157927 A | 7/2008 |
| JP | 4421756 B2 | 12/2009 |

(Continued)

OTHER PUBLICATIONS

Fujita et al., JP2016136144A, English translation, 2016 (Year: 2016).*

(Continued)

*Primary Examiner* — Shizhi Qian
(74) *Attorney, Agent, or Firm* — MATTINGLY & MALUR, PC

(57)　　　　ABSTRACT

A gas sensor element includes a heating portion and a ceramic layer. The ceramic layer has a first and second face, and is configured to be heated by the heating portion. The ceramic layer has an open-hole portion extending therethrough in a thickness direction from the first face toward the second face and constituting a through-hole for electrically connecting the first face to the second face. The open-hole portion is demarcated by a first inner wall face, and a second inner wall defining a recessed portion that is recessed inward of the ceramic layer. With the ceramic layer having a thickness of 1, the length of the recessed portion to the most distal position thereof from a position on the first inner wall face that is closest to a center axis of the open-hole portion is 0.05 or more and 0.20 or less.

14 Claims, 8 Drawing Sheets

(56)     References Cited

FOREIGN PATENT DOCUMENTS

| JP | 2010034258 A | * | 2/2010 |
| JP | 2012-032380 A |  | 2/2012 |
| JP | 2016136144 A | * | 7/2016 |

OTHER PUBLICATIONS

Japanese Office Action received in corresponding Japanese Application No. 2022-048059 dated May 28, 2024.

* cited by examiner

73

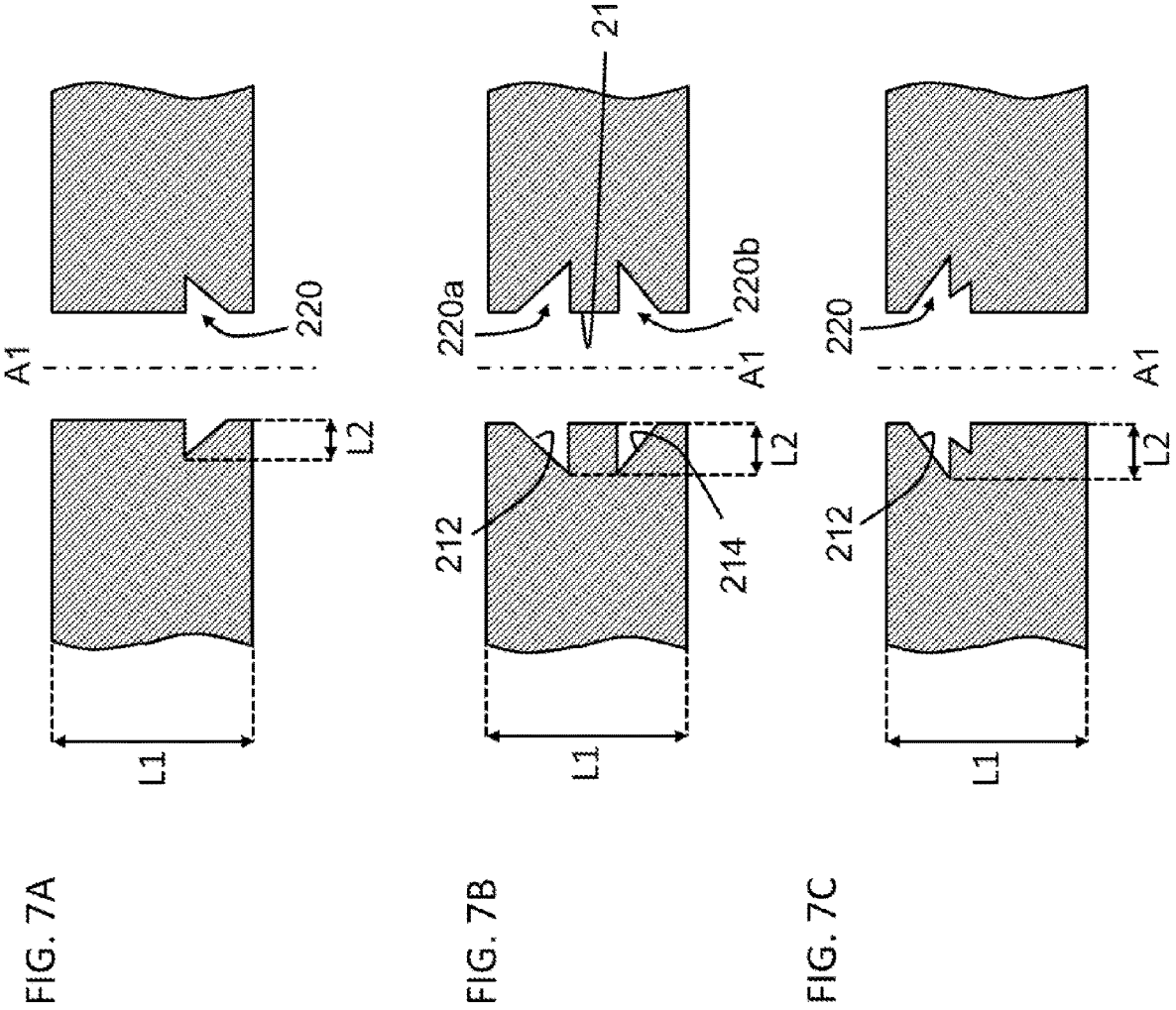

GAS SENSOR ELEMENT

CROSS REFERENCE TO RELATED APPLICATIONS

This application claims a priority to Japanese Patent Application No. 2022-048059 filed on Mar. 24, 2022, which is hereby incorporated by reference in its entirety.

FIELD OF INVENTION

The present invention relates to a gas sensor element.

BACKGROUND

Gas sensors are conventionally known that measure a gas component contained in a measurement target gas in, for example, an exhaust gas from an automobile. A gas sensor has a gas sensor element that includes a plurality of stacked ceramic layers and a detector formed on one end side in the lengthwise direction of the ceramic layers. This type of gas sensor element has a heater layer that includes a heating portion between ceramic layers. Conductive portions, such as a current-carrying terminal and a detection electrode, of the heating portion may be provided on one side and the other side of one or more ceramic layers. The ceramic layers have open-hole portions for electrically connecting these conductive portions in the thickness direction.

JP 2008-046112A discloses a gas sensor element that includes a first ceramic layer having a first open-hole portion and a second ceramic layer stacked on the first ceramic layer and having a second open-hole portion. This gas sensor element has a first conductive portion on an inner-circumferential face of the first open-hole portion, and a second conductive portion on an inner-circumferential face of the second open-hole portion, thereby achieving electrical contact between the first conductive portion and the second conductive portion. JP 4421756B discloses a gas sensor element that includes ceramic sheets each having a through-hole extending through front and back faces and a conductive pattern that allows the front and back faces to be electrically continuous. In this gas sensor element, an insulating paste is printed on an inner wall face of the through-hole, and a conductive layer paste is printed on the insulating paste so as to electrically connect the front and back faces.

JP 2008-046112A and JP 4421756B are examples of related art.

SUMMARY OF THE INVENTION

A gas sensor element with a configuration such as that disclosed in JP 2008-046112A may have a gap between the inner-circumferential face of the open-hole portion and the conductive portion. If a liquid component, such as moisture, present in the gap moves along the heater layer, reaches the heating portion or a region therearound, and is evaporated by the heat from the heating portion to become water vapor or the like, the pressure locally increases. This may cause delamination in the internal structure of the gas sensor element, resulting in damage to the gas sensor element. The same also applies to gas sensor elements with a configuration such as that disclosed in JP 4421756B. That is, similar delamination may occur if a liquid component present between the inner-circumferential face of the open-hole portion and the insulating paste moves along the insulating paste and the heater layer, reaches the heating portion or a region therearound, and evaporates with a temperature increase in the surrounding region, thus locally increasing the pressure. In such cases where the ceramic that forms the inner-circumferential face of the open-hole portion and the member printed on the inner-circumferential face or filling the open-hole portion are different in material, a gap between the inner-circumferential face and the printed (filling) member may lead to damage to the gas sensor element due to moisture, which can cause delamination, entering the gap.

In one aspect, the present invention has been made in view of the foregoing circumstances, and aims to provide a gas sensor element in which a gap is unlikely to occur between an inner wall face of an open-hole portion formed in a ceramic layer and a material in contact with the inner wall face.

To solve the above-stated problem, the invention adopts the following configurations.

A gas sensor element according to a first viewpoint of the present invention includes a heating portion and a ceramic layer. The ceramic layer has a first face and a second face on an opposite side to the first face, and is configured to be heated by the heating portion. The ceramic layer has an open-hole portion extending therethrough in a thickness direction from the first face toward the second face and constituting a through-hole for electrically connecting the first face to the second face. The open-hole portion is demarcated by a first inner wall face extending in the thickness direction, and a second inner wall face continuous with the first inner wall face and defining a recessed portion that is recessed inward of the ceramic layer relative to the first inner wall face. With the ceramic layer having a thickness of 1, the length of the recessed portion to the most distal position thereof from a position on the first inner wall face that is closest to a center axis of the open-hole portion is 0.05 or more and 0.20 or less.

According to the first viewpoint, a recessed portion that is recessed inward of the ceramic layer is formed in the open-hole portion for the through-hole that extends through the ceramic layer in the thickness direction. The largest depth of the recessed portion from the position closest to the center axis of the open-hole portion relative to the thickness of the ceramic layer is 0.05 or more and 0.15 or less. This improves the adhesion between the first and second inner wall faces of the ceramic that demarcate the open-hole portion and a different material when the through-hole is formed with the ceramic layers and the different material, making it unlikely for a gap to occur therebetween.

A gas sensor element according to a second viewpoint of the invention is the gas sensor element according to the first viewpoint wherein, with the ceramic layer having a thickness of 1, the length of the recessed portion to the most distal position thereof from the position on the first inner wall face that is closest to the center axis of the open-hole portion is 0.10 or more and 0.20 or less.

A gas sensor element according to a third viewpoint of the invention is the gas sensor element according to the first or second viewpoint wherein the second inner wall face is continuous over an entire circumference of the open-hole portion, and the recessed portion is defined by the second inner wall face so as to have an annular shape as viewed from the first face.

According to the third viewpoint, the recessed portion is continuous over the entire circumference of the open-hole portion about the center axis. This further improves adhesion between the ceramic and the different material.

A gas sensor element according to a fourth viewpoint of the invention is the gas sensor element according to any one of the first to third viewpoints wherein the second inner wall face is present at least either at a position closer to the first face or at a position closer to the second face in the thickness direction.

A gas sensor element according to a fifth viewpoint of the invention is the gas sensor element according to any one of the first to fourth viewpoints wherein a plurality of the second inner wall faces are present along the thickness direction.

A gas sensor element according to a sixth viewpoint of the invention is the gas sensor element according to any one of the first to fifth viewpoints further including a conductive portion having conductivity and filling an inside of the open-hole portion.

A gas sensor element according to a seventh viewpoint of the invention is the gas sensor element according to any one of the first to sixth viewpoints wherein the heating portion is arranged on the first face side of the ceramic layer, and the through-hole electrically connects the heating portion to an element on the second face side of the ceramic layer.

A gas sensor element according to an eighth viewpoint of the invention is the gas sensor element according to any one of the first to seventh viewpoints wherein the gas sensor element is configured to measure a concentration of nitrogen oxide in a measurement target gas.

According to the present invention, a gas sensor element is provided in which a gap is unlikely to occur between an inner wall face of an open-hole portion formed in a ceramic layer and a different material in contact with the inner wall face, thereby making it unlikely for delamination to occur in the internal structure.

BRIEF DESCRIPTION OF THE DRAWINGS

FIG. 7A is a partial cross-sectional view of a region around an open-hole portion according to a variation.

FIG. 7B is a partial cross-sectional view of a region around an open-hole portion according to a variation.

FIG. 7C is a partial cross-sectional view of a region around an open-hole portion according to a variation.

EMBODIMENT OF THE INVENTION

Hereinafter, an embodiment according to one aspect of the present invention (hereinafter also referred to as "the present embodiment") will be described with reference to the drawings. Note that the present embodiment described below is merely illustrative of the present invention in all respects. It goes without saying that various improvements and modifications can be made without departing from the scope of the present invention. In other words, in the practice of the present invention, specific configurations suitable for embodiments may be employed as appropriate. Note that constituent elements shown in the diagrams may be deformed for convenience of description and do not necessarily show the actual size relationship between them.

1. Configuration of Gas Sensor Element

Figure 1:
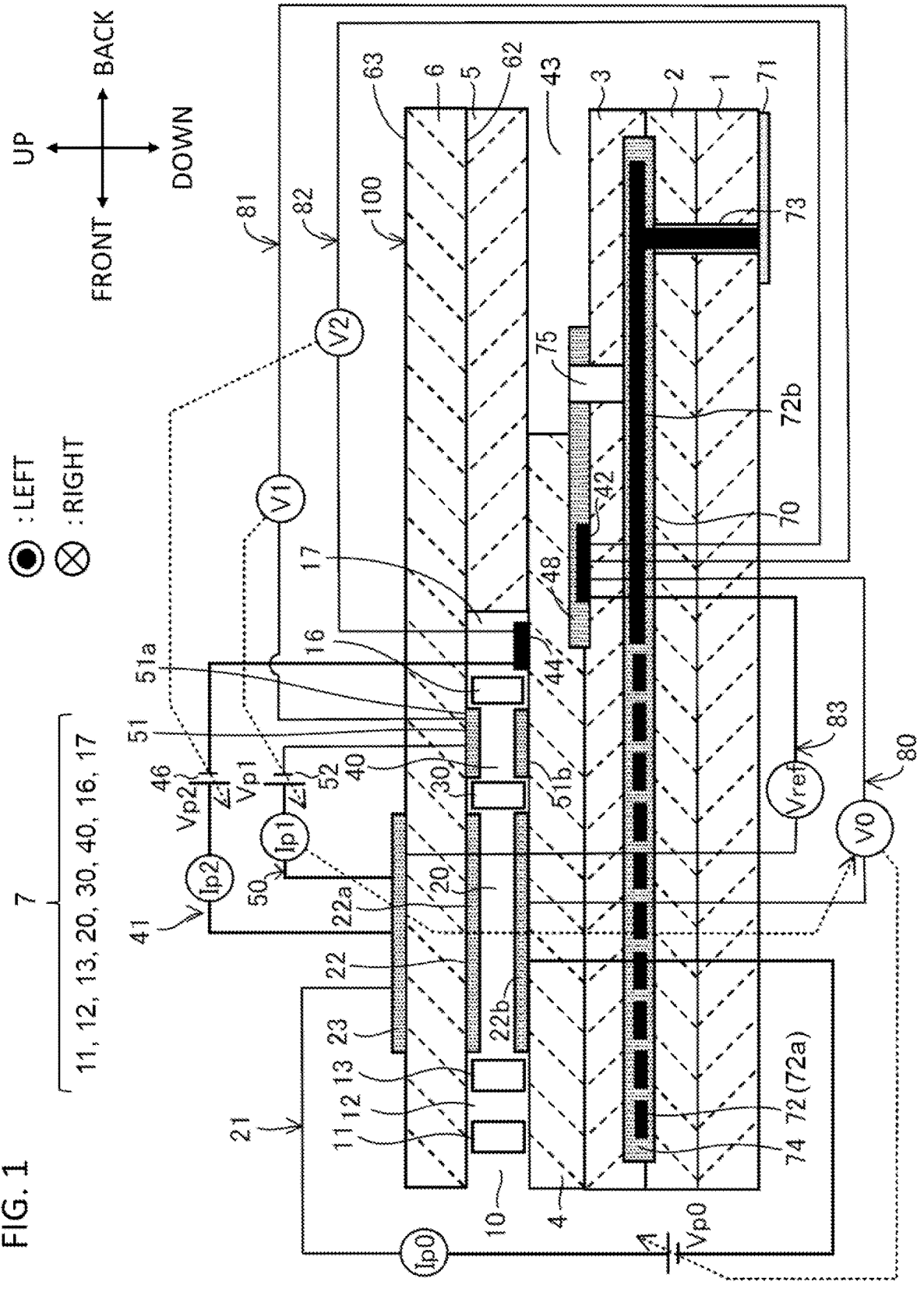
FIG. 1 is a schematic cross-sectional view schematically showing the configuration of a sensor element according to one embodiment.

FIG. 1 is a schematic cross-sectional view schematically showing an example of the configuration of a gas sensor element 100 according to the present embodiment. The gas sensor element 100 is shaped as an elongated plate-like body that extends along the lengthwise direction, for example, and has a rectangular parallelepiped shape, for example. The gas sensor element 100 illustrated in FIG. 1 includes a front end portion and a rear end portion as end portions in the lengthwise direction, and in the following description, the front end portion is the left end portion in FIG. 1 and the rear end portion is the right end portion in FIG. 1. The direction from the proximal to distal side of the paper plane of FIG. 1 is the left-right direction of the gas sensor element 100, as shown in FIG. 1. However, the shape of the gas sensor element 100 is not limited to this example, and may be appropriately selected in accordance with the mode of implementation. The orientation of the gas sensor element 100 when in use is not limited to the orientation defined in FIG. 1.

The gas sensor element 100 has a structure in which six layers, namely, a first substrate layer 1, a second substrate layer 2, a third substrate layer 3, a first solid electrolyte layer 4, a spacer layer 5, and a second solid electrolyte layer 6 are stacked in this order from the lower side in the cross-section of FIG. 1. In other words, the gas sensor element 100 includes a laminate constituted by the first solid electrolyte layer 4, the second solid electrolyte layer 6, and the spacer layer 5. The solid electrolytes forming the six layers (i.e., the first substrate layer 1, the second substrate layer 2, the third substrate layer 3, the first solid electrolyte layer 4, the spacer layer 5, and the second solid electrolyte layer 6) may be dense. Here, being "dense" means having a porosity of 5% or less.

The gas sensor element 100 is produced by performing steps such as predetermined processing and printing of wiring patterns on ceramic green sheets corresponding to the respective layers, for example, stacking the resultant layers, and then integrating them through firing. In one example, the gas sensor element 100 is a laminate constituted by a plurality of ceramic layers. In the following, the layers 1 to 6 may be referred to as "ceramic layers" without distinction. In the present embodiment, the upper face of the second solid electrolyte layer 6 forms the upper face of the gas sensor element 100, the lower face of the first substrate layer 1 forms the lower face of the gas sensor element 100, and side faces of the layers 1 to 6 form side faces of the gas sensor element 100.

Target Gas Flow Portion

In the front end portion of the gas sensor element 100, a gas introduction opening 10, a first diffusion control portion 11, a buffer space 12, a second diffusion control portion 13, a first internal cavity 20, a third diffusion control portion 30, a second internal cavity 40, a fourth diffusion control portion 16, and a third internal cavity 17 are arranged adjacent to each other in this order in a connected manner between the lower face of the second solid electrolyte layer 6 and the upper face of the first solid electrolyte layer 4.

The gas introduction opening 10, the buffer space 12, the first internal cavity 20, the second internal cavity 40, and the third internal cavity 17 are spaces provided by removing portions of the spacer layer 5, and more specifically are spaces inside the gas sensor element 100 (internal spaces) defined on the upper side by the lower face of the second solid electrolyte layer 6 and defined on the lower side by the upper face of the first solid electrolyte layer 4.

The first diffusion control portion 11 is provided as two laterally elongated slits (the long sides of the openings thereof extending along a direction perpendicular to the plane of the drawing). Also, the second diffusion control portion 13, the third diffusion control portion 30, and the fourth diffusion control portion 16 are provided as holes whose lengths along a direction perpendicular to the plane of the drawing are shorter than the first internal cavity 20, the second internal cavity 40, and the third internal cavity 17, respectively.

As illustrated in FIG. 1, the second diffusion control portion 13, the third diffusion control portion 30, and the fourth diffusion control portion 16 may each be provided as two laterally elongated slits (the long sides of the openings thereof extending along a direction perpendicular to the plane of the drawing), similarly to the first diffusion control portion 11, but are not limited thereto. For example, the fourth diffusion control portion 16 may be provided as one laterally elongated slit (the lengthwise direction of the opening thereof extending along a direction perpendicular to the plane of the drawing) formed as a gap defined on one side by the lower face of the second solid electrolyte layer 6. In other words, the fourth diffusion control portion 16 may be in contact with the upper face of the first solid electrolyte layer 4. The second diffusion control portion 13, the third diffusion control portion 30, and the fourth diffusion control portion 16 will each be described later. A portion (internal space) extending from the gas introduction opening 10 to the third internal cavity 17 will be referred to as a target gas flow portion 7.

Reference Gas Introduction Space

A reference gas introduction space 43 having side portions defined by side faces of the first solid electrolyte layer 4 is provided between the upper face of the third substrate layer 3 and the lower face of the spacer layer 5, at a position that is farther from the front end side (front side of the gas sensor element 100) than the target gas flow portion 7 is. A reference gas such as air is introduced into the reference gas introduction space 43. Note that the configuration of the gas sensor element 100 need not be limited to this example. In another example, the first solid electrolyte layer 4 may be configured to extend to the rear end of the gas sensor element 100, and the reference gas introduction space 43 may be omitted. In this case, an air introduction layer 48 may be configured to extend to the rear end of the gas sensor element 100.

Air Introduction Layer

The air introduction layer 48 is a layer made of porous alumina and is configured such that reference gas is introduced thereto via the reference gas introduction space 43. In addition, the air introduction layer 48 is formed so as to cover a reference electrode 42.

Reference Electrode

The reference electrode 42 is formed so as to be held between the first solid electrolyte layer 4 and the upper face of the third substrate layer 3, and is surrounded by the air introduction layer 48 that is connected to the reference gas introduction space 43. The reference electrode 42 is used to measure the oxygen concentration (oxygen partial pressure) in the first internal cavity 20, the second internal cavity 40, and the third internal cavity 17. This will be described in detail below.

Gas Introduction Opening

The gas introduction opening 10 is a portion of the target gas flow portion 7 that is open to the external space. A target gas in the external space is taken into the gas sensor element 100 through the gas introduction opening 10. In the present embodiment, as illustrated in FIG. 1, the gas introduction opening 10 is arranged in the front side face of the gas sensor element 100. In other words, the target gas flow portion 7 has an opening at a front end portion of the gas sensor element 100. However, it is not essential that the target gas flow portion 7 is configured to have an opening in the front side face of the gas sensor element 100, or in other words, that the gas introduction opening 10 is arranged in the front side face of the gas sensor element 100. The gas sensor element 100 need only be able to introduce a target gas from the external space into the target gas flow portion 7, and the gas introduction opening 10 may be arranged in the right side face or the left side face of the gas sensor element 100, for example.

When the gas introduction opening 10 is arranged in the front side face of the gas sensor element 100, the target gas flow portion 7 may be blocked by a dense ceramic layer at the side faces (right side face and left side face) of the gas sensor element 100. The ceramic layer may be made of a material such as zirconia ($ZrO_2$). If the target gas flow portion 7 is blocked by a dense ceramic layer at the side faces of the gas sensor element 100, the gas sensor element 100 is configured such that a target gas in the external space is introduced into the gas sensor element 100 through the gas introduction opening 10.

However, in the gas sensor element 100, it is not essential that the target gas flow portion 7 is blocked by a dense ceramic layer at the side faces of the gas sensor element 100. Also, it is not essential that the gas sensor element 100 includes the gas introduction opening 10. In other words, in the gas sensor element 100, it is sufficient that a target gas in the external space can be introduced into the target gas flow portion 7, and it is not essential that the target gas in the external space is introduced through the gas introduction opening 10. For example, the gas sensor element 100 may have a configuration in which at least one of the side faces of the spacer layer 5 is open instead of being blocked by a dense ceramic layer, such that the target gas in the external space can be introduced into the target gas flow portion 7 without provision of the gas introduction opening 10.

First Diffusion Control Portion

The first diffusion control portion 11 is a region that applies predetermined diffusion resistance to the measurement target gas introduced from the gas introduction opening 10.

Buffer Space

The buffer space 12 is a space that is provided in order to guide the measurement target gas, which was introduced from the first diffusion control portion 11, to the second diffusion control portion 13.

Second Diffusion Control Portion

The second diffusion control portion 13 is a region that applies predetermined diffusion resistance to the measurement target gas that is to be introduced from the buffer space 12 into the first internal cavity 20.

When the measurement target gas outside of the gas sensor element 100 is introduced into the first internal cavity 20, the measurement target gas, which has been rapidly introduced through the gas introduction opening 10 into the gas sensor element 100 due to a change in the pressure in the measurement target gas in the external space (a pulsation of the exhaust pressure in the case in which the measurement target gas is exhaust gas of an automobile), is not directly introduced into the first internal cavity 20, but rather is introduced into the first internal cavity 20 after passing through the first diffusion control portion 11, the buffer space 12, and the second diffusion control portion 13 where fluctuation in the concentration of the measurement target gas is canceled. Accordingly, fluctuation in the concentration of the measurement target gas introduced into the first internal space is reduced to be almost negligible.

First Internal Cavity

The first internal cavity 20 is provided as a space for adjusting the oxygen partial pressure in the measurement target gas introduced via the second diffusion control portion 13. The oxygen partial pressure is adjusted by operation of a main pump cell 21.

Main Pump Cell

The main pump cell 21 is an electro-chemical pump cell constituted by the internal pump electrode 22, the external pump electrode 23, and the second solid electrolyte layer 6 that is sandwiched by these electrodes. The internal pump electrode 22 has a ceiling electrode portion 22a provided on substantially the entirety of a lower face 62 of the second solid electrolyte layer 6 adjoining (facing) the first internal cavity 20. The external pump electrode 23 is provided in a region of an upper face 63 of the second solid electrolyte layer 6 that corresponds to the ceiling electrode portion 22a so as to adjoin the external space.

The internal pump electrode 22 is formed so as to extend across the upper and lower solid electrolyte layers that define the first internal cavity 20 (i.e., the second solid electrolyte layer 6 and the first solid electrolyte layer 4), and the spacer layer 5 that forms side walls. Specifically, the ceiling electrode portion 22a is formed on the lower face 62 of the second solid electrolyte layer 6 that forms the ceiling face of the first internal cavity 20, and a bottom electrode portion 22b is formed on the upper face of the first solid electrolyte layer 4 that forms the bottom face. Side electrode portions (not shown) that connect the ceiling electrode portion 22a and the bottom electrode portion 22b are formed on side wall faces (inner faces) of the spacer layer 5 that forms the two side wall portions of the first internal cavity 20. In other words, the internal pump electrode 22 is provided in the form of a tunnel at the region in which the side electrode portions are arranged.

The internal pump electrode 22 and the external pump electrode 23 are formed as porous cermet electrodes (for example, cermet electrodes formed using $ZrO_2$ and Pt containing 1% Au). Note that the internal pump electrode 22, which comes into contact with the measurement target gas, is made of a material that has a lowered capability of reducing a nitrogen oxide ($NO_x$) component in the measurement target gas.

The gas sensor element 100 is configured such that the main pump cell 21 can apply a desired pump voltage Vp0 between the internal pump electrode 22 and the external pump electrode 23, thereby causing a pump current Ip0 to flow in the positive direction or the negative direction between the internal pump electrode 22 and the external pump electrode 23, so that oxygen in the first internal cavity 20 is pumped out to the external space, or oxygen in the external space is pumped into the first internal cavity 20.

Oxygen Partial Pressure Detection Sensor Cell for Main Pump Control

Furthermore, in order to detect the oxygen concentration (oxygen partial pressure) in the atmosphere in the first internal cavity 20, the internal pump electrode 22, the second solid electrolyte layer 6, the spacer layer 5, the first solid electrolyte layer 4, the third substrate layer 3, and the reference electrode 42 constitute an oxygen partial pressure detection sensor cell 80 for main pump control (i.e., an electro-chemical sensor cell).

The gas sensor element 100 is configured to be capable of identifying the oxygen concentration (oxygen partial pressure) in the first internal cavity 20 by measuring an electromotive force V0 in the oxygen partial pressure detection sensor cell 80 for main pump control. Furthermore, the pump current Ip0 is controlled by performing feedback control on Vp0 such that the electromotive force V0 is kept constant. Accordingly, the oxygen concentration in the first internal cavity 20 can be kept at a predetermined constant value.

Third Diffusion Control Portion

The third diffusion control portion 30 is a region that applies predetermined diffusion resistance to the measurement target gas whose oxygen concentration (oxygen partial pressure) has been controlled through operation of the main pump cell 21 in the first internal cavity 20, thereby guiding the measurement target gas to the second internal cavity 40.

Second Internal Cavity

The second internal cavity 40 is provided as a space for further adjusting the oxygen partial pressure in the measurement target gas that has been introduced through the third diffusion control portion 30. The oxygen partial pressure is adjusted through operation of the auxiliary pump cell 50.

Auxiliary Pump Cell

The auxiliary pump cell 50 is an auxiliary electro-chemical pump cell constituted by an auxiliary pump electrode 51, the external pump electrode 23 (which is not limited to the external pump electrode 23, and may be any appropriate electrode outside the gas sensor element 100), and the second solid electrolyte layer 6. The auxiliary pump electrode 51 has a ceiling electrode portion 51a provided on substantially the entirety of the lower face of the second solid electrolyte layer 6 facing the second internal cavity 40.

The auxiliary pump electrode 51 with this configuration is arranged inside the second internal cavity 40 in the form of a tunnel similarly to the above-described internal pump electrode 22 provided inside the first internal cavity 20. That is to say, the ceiling electrode portion 51a is formed on the lower face 62 of the second solid electrolyte layer 6 that forms the ceiling face of the second internal cavity 40, and a bottom electrode portion 51b is formed on the upper face of the first solid electrolyte layer 4 that forms the bottom face of the second internal cavity 40. Side electrode portions (not shown) that connect the ceiling electrode portion 51a and the bottom electrode portion 51b are formed on two wall faces of the spacer layer 5 that form side walls of the second internal cavity 40. Thus, the auxiliary pump electrode 51 is in the form of a tunnel.

Note that the auxiliary pump electrode 51 is also made of a material that has a lowered capability of reducing a nitrogen oxide component in the measurement target gas, similarly to the internal pump electrode 22.

The gas sensor element 100 is configured such that the auxiliary pump cell 50 can apply a desired voltage Vp1 between the auxiliary pump electrode 51 and the external pump electrode 23, so that oxygen in the atmosphere in the second internal cavity 40 is pumped out to the external space, or oxygen is pumped from the external space into the second internal cavity 40.

Oxygen Partial Pressure Detection Sensor Cell for Auxiliary Pump Control

Furthermore, in order to control the oxygen partial pressure in the atmosphere in the second internal cavity 40, the auxiliary pump electrode 51, the reference electrode 42, the second solid electrolyte layer 6, the spacer layer 5, the first solid electrolyte layer 4, and the third substrate layer 3 constitute an oxygen partial pressure detection sensor cell 81 for auxiliary pump control (i.e., an electro-chemical sensor cell).

Note that the auxiliary pump cell 50 performs pumping using a variable power source 52 whose voltage is controlled based on an electromotive force V1 detected by the oxygen partial pressure detection sensor cell 81 for auxiliary pump control. Accordingly, the oxygen partial pressure in the atmosphere in the second internal cavity 40 is controlled to be a partial pressure that is low enough to substantially not affect the $NO_x$ measurement.

Furthermore, a pump current Ip1 is used to control the electromotive force of the oxygen partial pressure detection sensor cell 80 for main pump control. Specifically, the pump current Ip1 is input as a control signal to the oxygen partial pressure detection sensor cell 80 for main pump control, and the electromotive force V0 is controlled so as to keep a constant gradient of the oxygen partial pressure in the measurement target gas that is introduced from the third diffusion control portion 30 into the second internal cavity 40. In the case where the sensor is used as a $NO_x$ sensor, the oxygen concentration in the second internal cavity 40 is kept at a constant value of around 0.001 ppm through operation of the main pump cell 21 and the auxiliary pump cell 50.

Fourth Diffusion Control Portion

The fourth diffusion control portion 16 is a region that applies predetermined diffusion resistance to the measurement target gas whose oxygen concentration (oxygen partial pressure) has been controlled through operation of the auxiliary pump cell 50 in the second internal cavity 40, thereby guiding the measurement target gas to the third internal cavity 17.

Third Internal Cavity

The third internal cavity 17 is provided as a space for performing processing regarding measurement of the concentration of nitrogen oxide ($NO_x$) in the measurement target gas that was introduced via the fourth diffusion control portion 16. The $NO_x$ concentration is measured by operation of a measurement pump cell 41. In this embodiment, the oxygen concentration (oxygen partial pressure) is adjusted in the first internal cavity 20, and thereafter, the auxiliary pump cell 50 further adjusts, in the second internal cavity 40, the oxygen partial pressure in the measurement target gas that was introduced through the third diffusion control portion 30. The oxygen concentration in the measurement target gas that is introduced from the second internal cavity 40 into the third internal cavity 17 can thus be kept constant with high accuracy. This enables the gas sensor element 100 according to this embodiment to measure the $NO_x$ concentration with high accuracy.

Measurement Pump Cell

The measurement pump cell 41 measures the concentration of nitrogen oxide in the measurement target gas, in the third internal cavity 17. The measurement pump cell 41 is an electro-chemical pump cell constituted by a measurement electrode 44, the external pump electrode 23, the second solid electrolyte layer 6, the spacer layer 5, and the first solid electrolyte layer 4. The measurement electrode 44 in the example in FIG. 1 is provided on the upper face of the first solid electrolyte layer 4 adjoining (facing) the third internal cavity 17.

Measurement Electrode

The measurement electrode 44 is a porous cermet electrode. The measurement electrode 44 functions also as a $NO_x$ reduction catalyst for reducing $NO_x$ that is present in the atmosphere in the third internal cavity 17. In the example in FIG. 1, the measurement electrode 44 is exposed within the third internal cavity 17. In another example, the measurement electrode 44 may also be covered by a diffusion control portion. This diffusion control portion may be constituted by a porous film composed mainly of alumina ($Al_2O_3$). The diffusion control portion serves to restrict the amount of $NO_x$ flowing into the measurement electrode 44, and also functions as a protective film for the measurement electrode 44.

The gas sensor element 100 is configured such that the measurement pump cell 41 can pump out oxygen generated through decomposition of nitrogen oxide in the atmosphere around the measurement electrode 44, and can detect the amount of generated oxygen as a pump current Ip2.

Furthermore, in order to detect the oxygen partial pressure around the measurement electrode 44, the second solid electrolyte layer 6, the spacer layer 5, the first solid electrolyte layer 4, the third substrate layer 3, the measurement electrode 44, and the reference electrode 42 constitute an oxygen partial pressure detection sensor cell 82 for measurement pump control (i.e., an electro-chemical sensor cell). A variable power source 46 is controlled based on a voltage (an electromotive force) V2 detected by the oxygen partial pressure detection sensor cell 82 for measurement pump control.

The measurement target gas guided into the third internal cavity 17 reaches the measurement electrode 44 in a state in which the oxygen partial pressure has been controlled. Nitrogen oxide in the measurement target gas around the measurement electrode 44 is reduced to generate oxygen ($2NO \rightarrow N_2 + O_2$). The generated oxygen is pumped by the measurement pump cell 41, and, at that time, a voltage Vp2 of the variable power source is controlled such that the control voltage V2 detected by the oxygen partial pressure detection sensor cell 82 for measurement pump control is kept constant. The amount of oxygen generated around the measurement electrode 44 is proportional to the concentration of nitrogen oxide in the measurement target gas, and thus, it is possible to calculate the concentration of nitrogen oxide in the measurement target gas using the pump current Ip2 in the measurement pump cell 41.

Furthermore, if the measurement electrode 44, the first solid electrolyte layer 4, the third substrate layer 3, and the reference electrode 42 are combined to constitute an oxygen partial pressure detection means as an electro-chemical sensor cell, it becomes possible to detect an electromotive force that corresponds to a difference between the amount of oxygen generated through reduction of a $NO_x$ component in the atmosphere around the measurement electrode 44 and the amount of oxygen contained in reference air. This enables the measurement of the concentration of the nitrogen oxide component in the measurement target gas.

Sensor Cell

Furthermore, the second solid electrolyte layer 6, the spacer layer 5, the first solid electrolyte layer 4, the third substrate layer 3, the external pump electrode 23, and the reference electrode 42 constitute an electro-chemical sensor cell 83. The gas sensor element 100 is configured to be capable of detecting the oxygen partial pressure in the measurement target gas outside the sensor, based on an electromotive force Vref obtained by the sensor cell 83.

In the gas sensor element 100 having the above-described configuration, when the main pump cell 21 and the auxiliary pump cell 50 operate, the measurement target gas whose oxygen partial pressure is always kept at a constant low value (a value that substantially does not affect the $NO_x$ measurement) can be supplied to the measurement pump cell 41. Accordingly, the gas sensor element 100 is configured to be capable of identifying the nitrogen oxide concentration in the measurement target gas, based on the pump current Ip2 that flows when oxygen generated through reduction of $NO_x$ is pumped out by the measurement pump cell 41, substantially in proportion to the nitrogen oxide concentration in the measurement target gas.

Heater

The gas sensor element 100 also includes a heater 70 that serves to adjust temperature by heating the gas sensor element 100 and keep the temperature. Except for a later-described heater electrode 71, the heater 70 is arranged at a position closer to the lower face of the gas sensor element 100 than the upper face of the gas sensor element 100 in the thickness direction (up-down direction in FIG. 1) of the gas sensor element 100. However, the arrangement of the heater 70 need not be limited to this example and may be selected as appropriate in accordance with the mode of implementation.

The heater 70 mainly includes the heater electrode 71, a heating portion 72 (72a and 72b), a lead portion 73, and a heater insulating layer 74. In one example in FIG. 1, the heater 70 also includes a pressure release hole 75. As will be described later, the lead portion 73 is formed as a pair of through-holes that extends through the first substrate layer 1 and the second substrate layer 2 in the thickness direction so as to electrically connect the lower face of the first substrate layer 1 to the upper face of the second substrate layer 2 (see FIGS. 2 and 3).

The heater electrodes 71 are electrodes formed in contact with the lower face of the first substrate layer 1 (the lower face of the gas sensor element 100). Electricity can be supplied from the outside to the heating portion 72 via a lead portion 73 by connecting the heater electrodes 71 to an external power source.

The heating portion 72 is an electrical resistor that is held from below and above by the second substrate layer 2 and the third substrate layer 3, i.e., heating resistors provided between the second substrate layer 2 and the third substrate layer 3. The heating portion 72 is supplied electricity from a heater power source (not shown) provided outside of the gas sensor element 100 via an electricity flow path constituted by the heater electrodes 71 and the lead portion 73, thereby generating heat to heat the solid electrolyte that forms the gas sensor element 100 and retain the temperature thereof.

The heating portion 72 is made of Pt, or composed mainly of Pt. The heating portion 72 is buried in a predetermined area of the gas sensor element 100 on the side where the measurement target gas flow section 7 is located, and face the measurement target gas flow section 7 in the element thickness direction. The heating portion 72 has a thickness of about 10 μm to 20 μm, for example.

Figure 2:
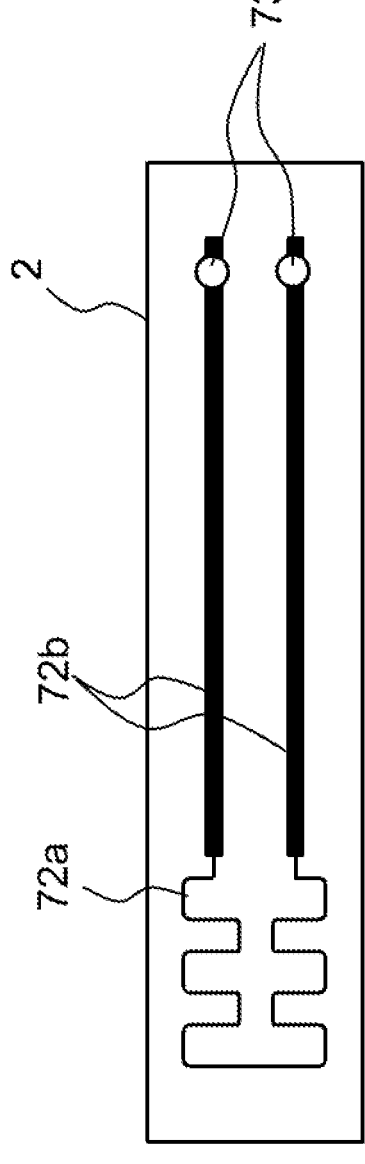
FIG. 2 is a schematic view showing an example of a schematic plan arrangement of a heating portion and a region therearound.
Figure 3:
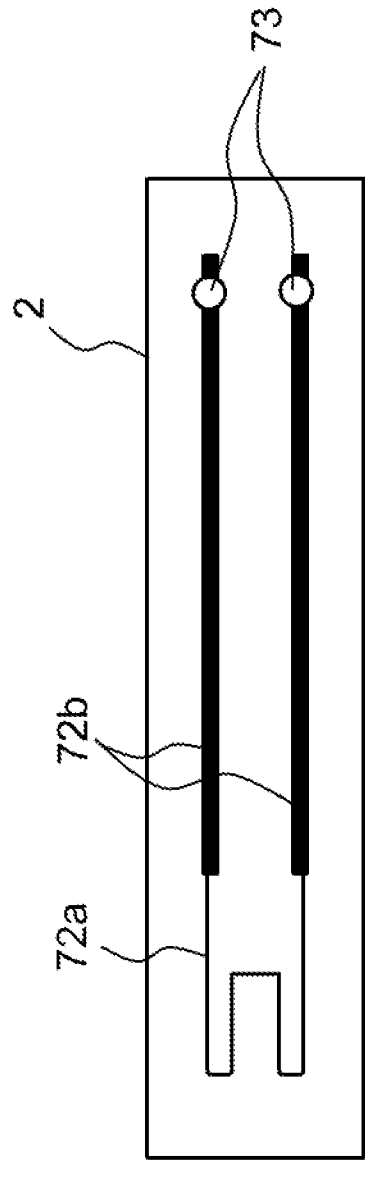
FIG. 3 is a schematic view showing another example of a schematic plan arrangement of a heating portion and a region therearound.

FIG. 2 is a schematic view showing an example of a schematic plan arrangement of the heating portion 72 and a region therearound. As shown in FIG. 2, the heating portions 72 has a meandering portion 72a that meanders on the front side of the gas sensor element 100, and a pair of linear portions 72b that linearly extends from two ends of the meandering portion 72a toward the rear end of the gas sensor element 100. Note that the shape of the meandering portion 72a is not limited to the example in FIG. 2, and may be, for example, the shape shown in FIG. 3. The two linear portions 72b have substantially the same shape, i.e., the same resistance value. The rear ends of the linear portions 72b are connected to the respective through-holes that constitute the lead portion 73.

The heating portion 72 is capable of adjusting the temperature of the entire gas sensor element 100 at a temperature that activates the solid electrolyte. That is, in the gas sensor element 100, each part of the gas sensor element 100 can be heated to a specific temperature and this temperature can be retained by causing a current to flow through the heating portion 72 via the heater electrodes 71 to heat the heating portion 72. Specifically, the gas sensor element 100 is heated such that the temperature of the solid electrolyte and the electrodes near the measurement target gas flow section 7 is about 700° C. to 900° C. (or 750° C. to 950° C.).

The heater insulating layer 74 is an insulating layer formed so as to cover the heating portion 72, e.g., an insulating layer that is formed on the upper and lower faces of the heating portion 72 and made of an insulator such as alumina ($Al_2O_3$). The heater insulating layer 74 is formed for the purpose of achieving electrical insulation properties between the second substrate layer 2 and the heating portion 72 and electrical insulation properties between the third substrate layer 3 and the heating portion 72. The heater insulating layer 74 has a thickness of about 70 μm to 110 μm and is located at a position separated from the leading end face and side faces of the gas sensor element 100 by about 200 μm to 700 μm. Note that the thickness of the heater insulating layer 74 need not be constant, and may be different between a location where the heating portion 72 is present and a location where the heating portion 72 is not present.

The pressure release hole 75 is a region that passes through the third substrate layer 3 and is in communication with the reference gas inlet space 43. The pressure release hole 75 is formed for the purpose of mitigating the increase in the internal pressure due to a temperature rise in the heater insulating layer 74. Note that the provision of the pressure release hole 75 is not essential, and the pressure release hole 75 need not be provided.

Through-Hole

Figure 4:
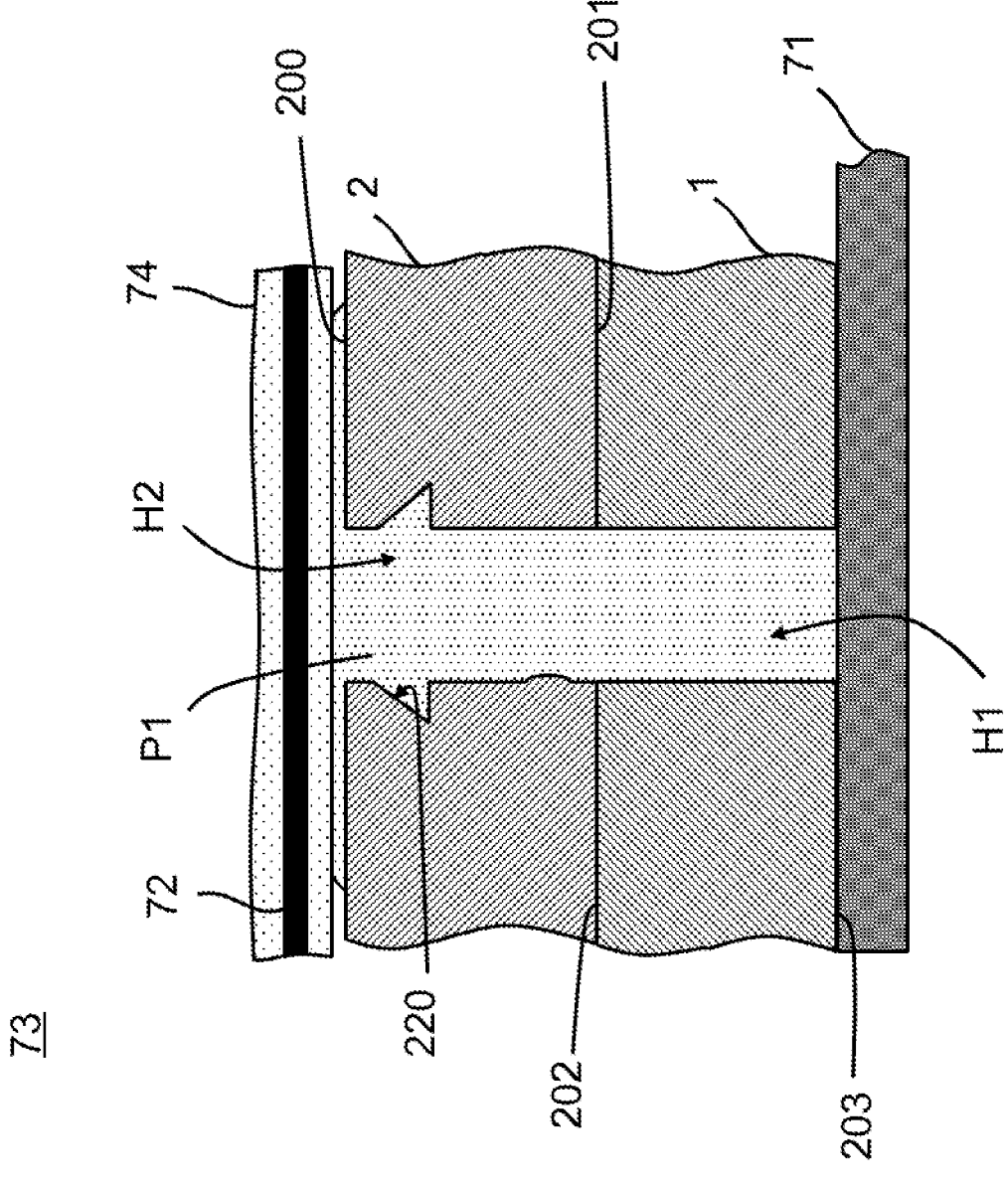
FIG. 4 is a partial cross-sectional view of a lead portion according to one embodiment.

FIG. 4 is a partial cross-sectional view showing the configuration of the lead portion 73 and a region therearound. The lead portion 73 in this embodiment is formed, without limitation thereto, as through-holes that electrically connect a lower face 203 of the first substrate layer 1 to an upper face 200 of the second substrate layer 2, i.e., electrically connect the lower face 203 to an upper face 202 of the first substrate layer 1 and electrically connects a lower face 201 to the upper face 200 of the second substrate layer 2. Each through-hole of this embodiment includes an open-hole portion H1 that extends through the first substrate layer 1, an open-hole portion H2 that extends through the second substrate layer 2, and a conductive portion P1 that fills the inside of the open-hole portions H1 and H2. The open-hole portion H1 extends through the first substrate layer 1 in the thickness direction from the upper face 202 toward the lower face 203 of the first substrate layer 1. The open-hole portion H2 extends through the second substrate layer 2 in the thickness direction from the upper face 200 toward the lower face 201 of the second substrate layer 2, and is in communication with the open-hole portion H1 with the first substrate layer 1 and the second substrate layer 2 being stacked on each other.

The conductive portion P1 may fill the inside of the open-hole portion H1 and be also continuous with a peripheral portion of the lower face 203 of the first substrate layer 1 that defines the open-hole portion H1. Similarly, the conductive portion P1 may fill the inside of the open-hole portion H2 and be also continuous with a peripheral portion of the upper face 200 of the second substrate layer 2 that defines the open-hole portion H2. This makes electrical connection between the heater electrode 71 and the pair of linear portions 72b of the heating portion 72 more reliable.

The conductive portion P1 is formed, without limitation thereto, by firing a conductive paste mainly composed of Pt together with ceramic green sheets corresponding to the first substrate layer 1 and the second substrate layer 2. In other words, the conductive portion P1 is integrally formed with the first substrate layer 1 and the second substrate layer 2. According to the inventors' study, gaps often occur between the conductive portion P1 and inner wall faces that demarcate the open-hole portions H1 and H2 due to a difference in the contraction rate between the conductive paste to serve as the conductive portion P1 and the ceramic green sheets when the conductive paste and the ceramic green sheets are heated and integrated. There are cases where a liquid component, such as moisture, enters these gaps from the outside of the gas sensor element 100. Since the heater insulating layer 74 is a porous body made of alumina or the like as mentioned above, the entering liquid component moves in the heater insulating layer 74 or along an interface thereof and reaches the heating portion 72 and a region therearound in some cases. The liquid component that has reached the heating portion 72 and the region therearound evaporates there and becomes water vapor or the like if the temperature therearound increases with heat generated by the heating portion 72. This locally increases the pressure and causes delamination in the internal structure, including the heater 70, of the gas sensor element 100, resulting in damage to the gas sensor element 100.

After diligent study, the inventors found that increasing the adhesion between the conductive portion P1 and the inner wall faces of the ceramic layers that demarcate the open-hole portions H1 and H2 and preventing liquid components from entering suppresses damage to the gas sensor element 100 caused by the entering of the liquid components. That is, the inventors found that the anchor effect between the ceramic green sheets and the conductive paste can be improved by forming at least one recessed portion within a predetermined depth range in the inner wall faces that demarcate the open-hole portions H1 and H2. This configuration may be applied to both the first substrate layer 1 and the second substrate layer 2, but may alternatively be applied to at least one of them. The following example describes application to the second substrate layer 2 and the open-hole portion H2. The upper face 200 and the lower face 201 of the second substrate layer 2 are examples of a first face and a second face, respectively, of the invention. Note that the following description can also be applied similarly to the first substrate layer 1 and the open-hole portion H1. In this case, the upper face 202 and the lower face 203 of the first substrate layer 1 are examples of the first face and the second face, respectively, of the invention.

Figure 5:
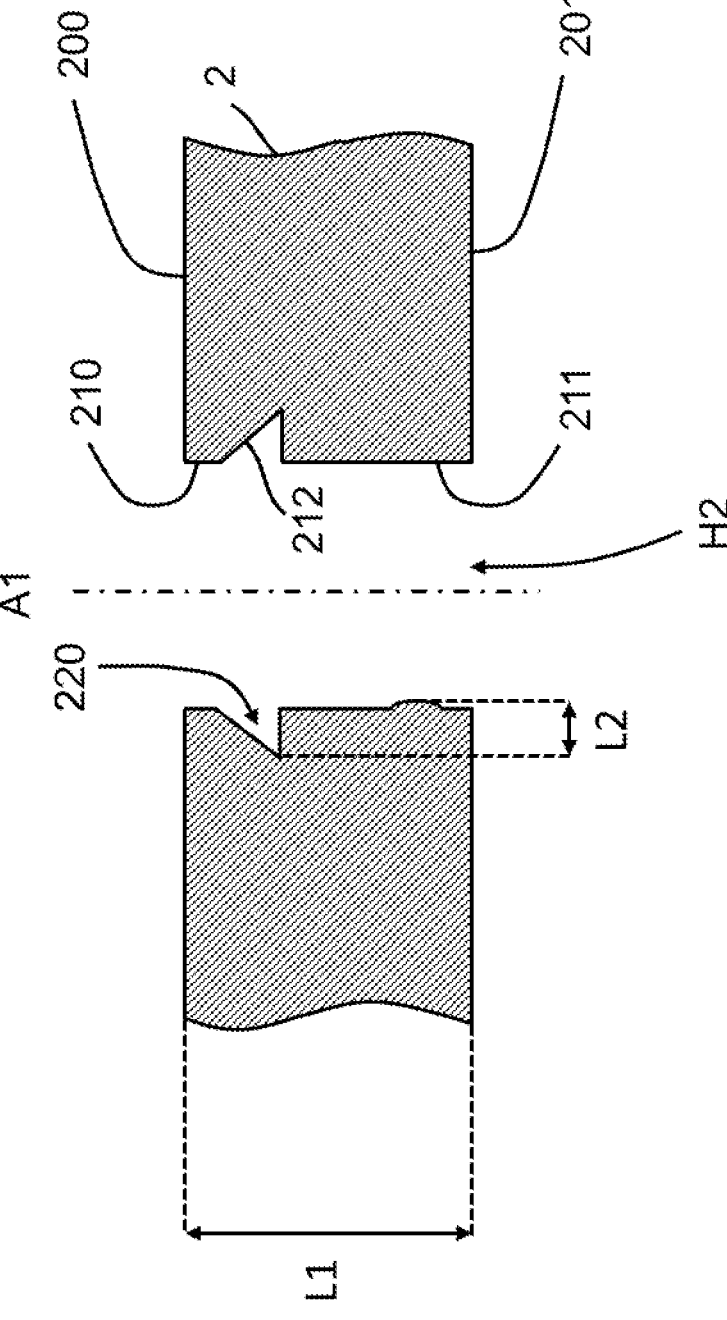
FIG. 5 is a partial cross-sectional view of a region around an open-hole portion according to one embodiment.

FIG. 5 is a cross-sectional view a region around the open-hole portion H2 of the second substrate layer 2. As mentioned above, the open-hole portion H2 extends through the second substrate layer 2 in the thickness direction from the upper face 200 toward the lower face 201. The shape of the open-hole portion H2 as viewed from the top of the second substrate layer 2 is not specifically limited, and may be substantially circular, elliptical, or rectangular, for example. A center axis A1 of the open-hole portion H2 refers to an axis passing through the geometric center of this shape and extending in the thickness direction of the second substrate layer 2.

In the example shown in FIG. 5, the open-hole portion H2 is demarcated by an upper first inner wall face 210, a second inner wall face 212 continuous with the upper first inner wall face 210, and a lower first inner wall face 211. The upper first inner wall face 210 and the lower first inner wall face 211 are faces extending substantially in the thickness direction of the second substrate layer 2. The upper first inner wall face 210 is continuous with the upper face 200, and the lower first inner wall face 211 is continuous with the lower face 201. The second inner wall face 212 is a face continuous with the upper first inner wall face 210 at an upper end and with the lower first inner wall face 211 at a lower end. The second inner wall face 212 defines a recessed portion 220 that is recessed inward of the second substrate layer 2 relative to the upper first inner wall face 210 and the lower first inner wall face 211. In this embodiment, the second inner wall face 212 is continuous in a fixed shape over the entire circumference of the open-hole portion H2 at a fixed position in the thickness direction of the second substrate layer 2. This defines, in the second inner wall face 212, the recessed portion 220 of this embodiment that has a substantially fixed depth over the entire circumference of the open-hole portion H2 and an annular shape as viewed from the top. However, the configuration of the second inner wall face 212 is not limited thereto. The shape of the second inner wall face 212 may change in the circumferential direction of the open-hole portion H2, or may be discontinuous rather than continuous over the entire circumference of the open-hole portion H2.

According to the inventors' study, the aforementioned anchor effect is effectively exhibited when, with the thickness L1 of the second substrate layer 2 being 1, the depth L2 of the recessed portion 220 to the most distal position is 0.05 or more and 0.20 or less, and the anchor effect is more effectively exhibited when the depth L2 is 0.10 or more and 0.20 or less. Here, the depth L2 of the recessed portion 220 to the most distal position refers to the largest depth of the recessed portion 220 that is identified from a position closest to the center axis A1 on the upper first inner wall face 210 and the lower first inner wall face 211 in a cross section of the second substrate layer 2 that includes the center axis A1 and is parallel to the lengthwise direction of the second substrate layer 2. The depth L2 relative to the thickness L1 is identified based on a cross-sectional picture of the second substrate layer 2 that is shot by an electron microscope (SU-1510 manufactured by Hitachi High-Tech Corporation). That is, it is possible to define as the depth L2 the distance between a pixel position identified as the position closest to the center axis A1 on the upper first inner wall face 210 and the lower first inner wall face 211 and a pixel position identified as the position farthest from the center axis A1 on the second inner wall face 212, in the aforementioned cross-sectional picture. Alternatively, it is also possible to define as the thickness L1 a value obtained by averaging distances in the thickness direction from pixel positions identified as being on the upper face 200 to pixel positions identified as being on the lower face 201 at randomly extracted 10 locations in the aforementioned cross-sectional picture.

Setting the largest depth of the recessed portion 220 in the above range allows the conductive paste for forming the conductive portion P1 to easily enter the recessed portion 220. Relative unevenness formed by the upper first inner wall face 210, the second inner wall face 212, and the lower first inner wall face 211 causes the anchor effect between the conductive paste and these wall faces, thus absorbing the difference in contraction between the ceramic layers and the conductive paste.

It is favorable, for a later-described reason, that one second inner wall face 212 is present at a position closer to either the upper face 200 or the lower face 201 in the thickness direction of the second substrate layer 2, without limitation thereto. That is, the second inner wall face 212 may be present at any position in the thickness direction of the second substrate layer 2 excluding positions continuous with the upper face 200 and positions continuous with the lower face 201. Further, two or more second inner wall faces 212 may be present in the thickness direction. The shape of the second inner wall face 212 (i.e., the shape of the recessed portion 220) in a cross-sectional view of the second substrate layer 2 is not specifically limited either, and may be selected as appropriate.

2. Method for Forming Through-Hole

The following is a description of one example of a method for producing the gas sensor element 100, including a method for forming a through-hole (lead portion 73) according to this embodiment, but the method for forming the lead portion 73 and the method for producing the gas sensor element 100 are not limited thereto.

First, as many ceramic green sheets to serve as the ceramic layers of the gas sensor element 100 as the ceramic layers of the gas sensor element 100 are prepared. In other words, six ceramic green sheets are prepared in this embodiment. The ceramic green sheets contain a solid electrolyte as a ceramic component, as mentioned above. All of the ceramic green sheets may have the same thickness, or may have different thicknesses depending on the layer to be formed.

Subsequently, an open-hole portion to be used for positioning during printing and stacking is formed in each of the six ceramic green sheets. The open-hole portion can be formed by punching each ceramic green sheet in the thickness direction using, for example, a punching device. The open-hole portion H1 of the first substrate layer 1 and the open-hole portion H2 of the second substrate layer 2 for the lead portion 73 may also be formed at this stage. If, for example, the aforementioned recessed portion 220 is formed in the second substrate layer 2, the open-hole portion H2 and the recessed portion 220 may be formed by punching the second substrate layer 2 once using a punching device capable of forming the upper first inner wall face 210, the lower first inner wall face 211, and the second inner wall face 212 by punching the second substrate layer 2 once. Alternatively, the recessed portion 220 may be formed by cutting an appropriate area of the inner wall face after forming, with the punching device, an open-hole portion demarcated by an inner wall face extending substantially in the thickness direction.

Next, necessary printing of a pattern and drying are performed on ceramic green sheets to serve as the third substrate layer 3, the first solid electrolyte layer 4, the spacer layer 5, and the second solid electrolyte layer 6. Printing can be performed by a known method, such as screen printing. Drying processing can also be performed by a known method.

Before, after, or in parallel to the above printing and drying processing, the open-hole portion H1 of the ceramic green sheet to serve as the first substrate layer 1 and the open-hole portion H2 of the ceramic green sheet to serve as the second substrate layer 2 are filled with a conductive paste to serve as the conductive portion P1. If the recessed portion 220 is present near the filling side at this time, the conductive paste more reliably enters the recessed portion 220, thus further improving the adhesion the conductive paste and the ceramic layer. This is the reason why it is favorable that one second inner wall face 212 is present at a position closer to either the upper face 200 or the lower face 201. This applies not only to the case where the second inner wall face 212 is formed in the ceramic green sheet to serve as the second substrate layer 2 but also the case where the second inner wall face is formed in the ceramic green sheet to serve as the first substrate layer 1.

Before, after, or in parallel to the aforementioned printing and drying processing, the heating portion 72 and the heater insulating layer 74 are formed on the upper face of the ceramic green sheet to serve as the second substrate layer 2. The heating portion 72 and the heater insulating layer 74 can be formed by printing a heater paste for forming the heating portion 72 (72a and 72b) and an insulating paste and drying these pastes. More specifically, the insulating paste is printed in a predetermined pattern and with a predetermined thickness on the surface, and is then dried. Subsequently, the heater paste is printed in a predetermined pattern and with a predetermined thickness on the insulating paste, and is then dried. Further, the insulating paste is printed in a predetermined pattern and with a predetermined thickness on the heater paste, and is then dried. The heater paste may be, for example, a Pt paste or a paste consisting mainly of Pt, and the insulating paste may be, for example, a paste consisting mainly of $Al_2O_3$.

After the printing of the pattern and drying for the six ceramic green sheets, these ceramic green sheets are positioned relative to each other, stacked in a predetermined order, and subjected to pressure bonding at a predetermined temperature and under a predetermined pressure condition. A laminate with six ceramic layers stacked is thus made. This laminate includes a plurality of unfired gas sensor elements 100. Individual gas sensor elements 100 are obtained by cutting this laminate and firing it at a predetermined firing temperature. Each of the thus-obtained gas sensor elements 100 has the lead portion 73 as a result of the conductive portion P1 being formed to fill the internal space of the open-hole portions H1 and H2.

3. Features

According to the above embodiment, the adhesion between the inner wall face that demarcates the open-hole portion for forming a through-hole and the conductive paste that fills the through-hole can be improved by a simple method. A gap can thus be prevented from occurring between the ceramic layer and the conductive portion, and internal elements of the gas sensor element 100 can be prevented from delaminating due to evaporation of a liquid component entering such a gap. Accordingly, a gas sensor element 100 that is unlikely to be damaged is provided.

4. Variations

Although an embodiment of the present invention has been described above, the description of the above embodiment is merely an illustration of the invention in all respects. Various improvements and variations may be made to the above embodiment. The constituent elements of the above embodiment may be omitted, replaced, and added as appropriate. The shape and dimensions of each constituent element of the above embodiment may be changed as appropriate, as per the mode of implementation. For example, the following changes are possible. Note that, in the following, the same constituent elements as those of the above embodiment are assigned the same reference numerals, and the description of the same features as the above embodiment is omitted as appropriate. The following variations can be combined as appropriate.

(1) The gas sensor element 100 of the above embodiment includes the first substrate layer 1. However, the first substrate layer 1 may be omitted, and the second substrate layer 2 may be the lowermost ceramic layer in FIG. 1.

Figure 6:
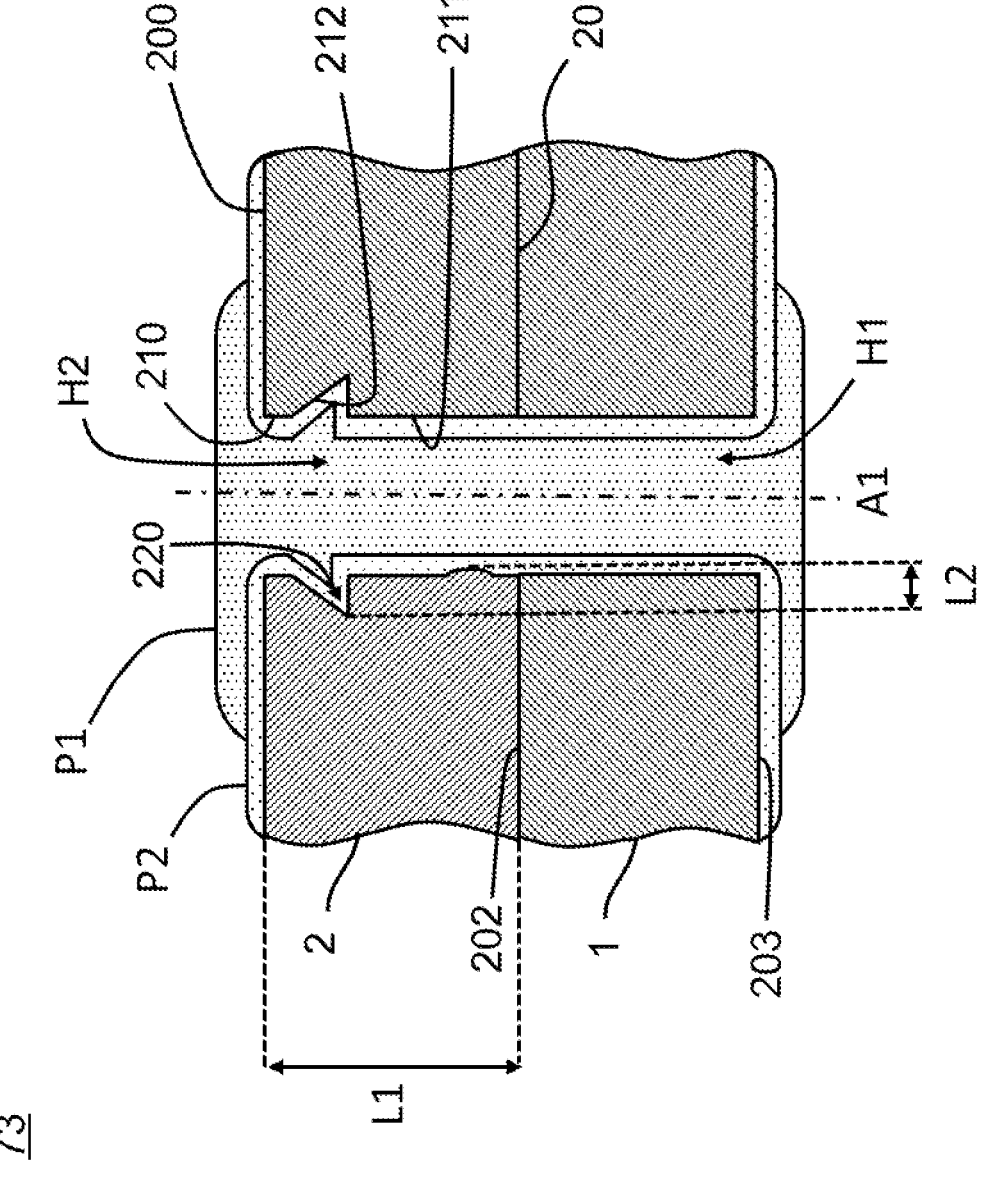
FIG. 6 is a partial cross-sectional view of a region around an open-hole portion according to another embodiment.

(2) The open-hole portions H1 and H2 are not necessarily filled with the conductive paste of the above embodiment. For example, the lead portion 73 may alternatively be formed by covering the inner wall faces of the open-hole portions H1 and H2 with an insulating paste P2 and filling the open-hole portions H1 and H2 with a conductive paste to serve as the conductive portion P1, as shown in FIG. 6.

In this case as well, a gap is unlikely to occur between the ceramic layer and the insulating paste P2, which is a different material, by forming an open-hole portion with a recessed portion in at least either the first substrate layer 1 or the second substrate layer 2. The effect of avoiding delamination caused by evaporation of a liquid component can thus be exhibited. Since the conductive paste and the insulating paste P2 are highly adhesive to each other, it is more important to prevent a gap from occurring between the ceramic layer and the area that comes in contact therewith and is formed with a different material.

Figures 7D, 7E:
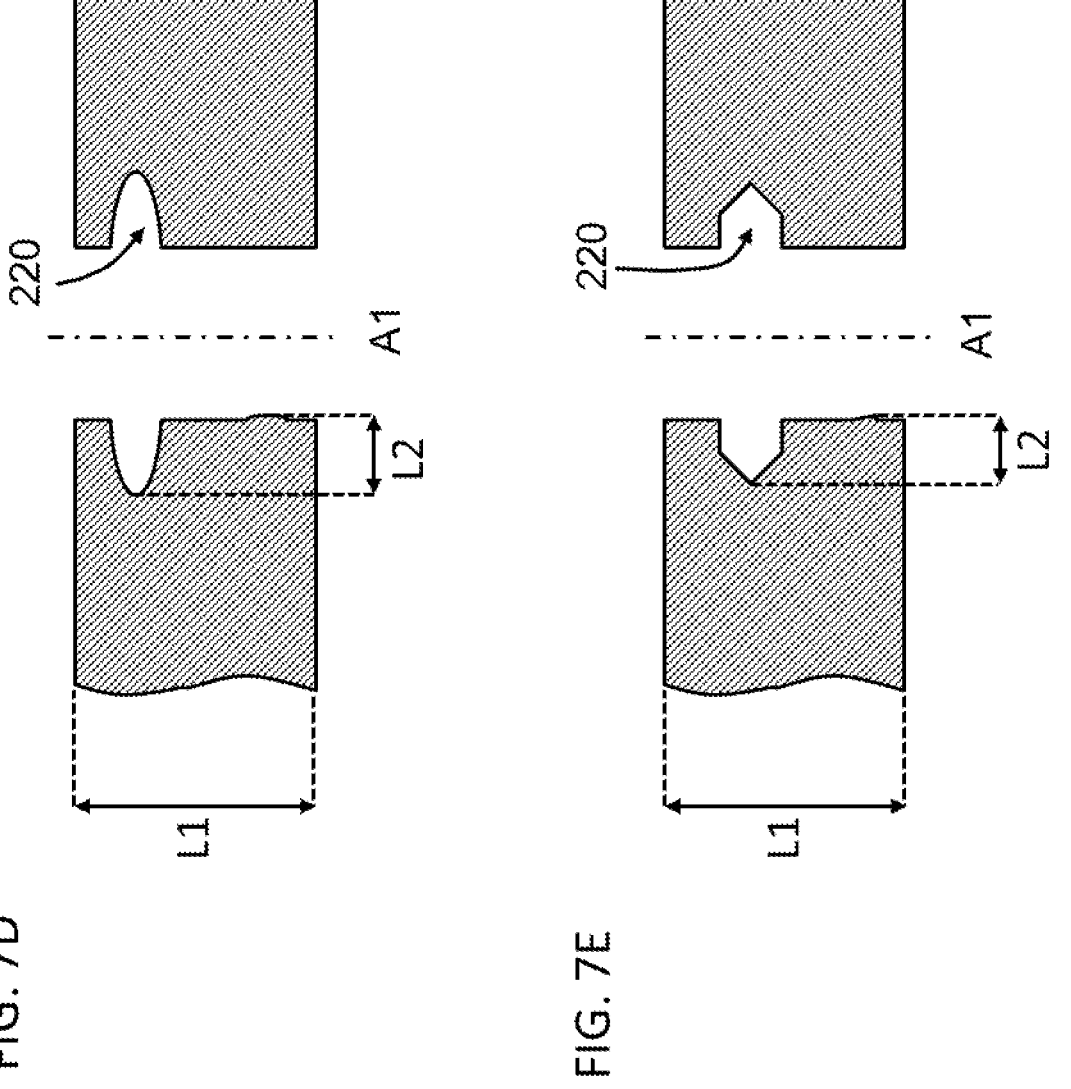
FIG. 7D is a partial cross-sectional view of a region around an open-hole portion according to a variation.
FIG. 7E is a partial cross-sectional view of a region around an open-hole portion according to a variation.
Figure 8:
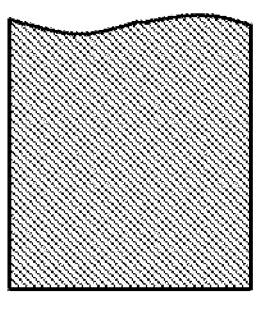
FIG. 8 is a partial cross-sectional view of a region around an open-hole portion according to a comparative example.
Figure 8:
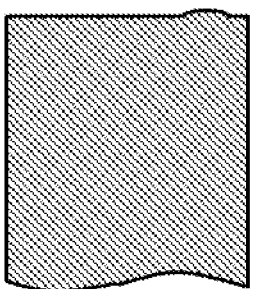

(3) The cross-sectional shape of the inner wall face demarcating the open-hole portion H2 (H1) is not limited to the shape described in the above embodiment, and may be changed as appropriate. For example, the cross-sectional shape of the inner wall face of the open-hole portion H2 (H1) can be a shape that defines a recessed portion 220 or recessed portions 220a and 220b, as shown in FIGS. 7A to 7E. In any case, the depth L2 can be specified in the same manner as in the above embodiment. FIG. 7A shows an example where a recessed portion 220 having substantially the same cross-sectional shape as that of the above embodiment is formed at a position closer to the lower face, rather than the upper face, of the ceramic layer. FIG. 7B shows an example where a recessed portion 220a and a recessed portion 220b are formed on the upper face side and lower face side, respectively, of the ceramic layer. In this case, an upper second inner wall face 212 can define the recessed portion 220a, and a lower second inner wall face 214 can define the recessed portion 220b. A first inner wall face that is continuous, at respective ends, with the upper second inner wall face 212 and the lower second inner wall face 214 may be referred to as an intermediate first inner wall face 213.

FIGS. 7C to 7E show examples of recessed portions 220 having different cross-sectional shapes. As shown in FIG. 7C, the second inner wall face 212 itself may have an uneven shape in a cross-sectional view. As shown in FIG. 7D, the cross-sectional shape of the recessed portion 220 may be a smoothly curved shape, rather than a shape with corners. Further, as shown in FIG. 7E, the cross-sectional shape of the recessed portion 220 may have a plurality of corners. In any of the cases illustrated in FIGS. 7C to 7E, the recessed portion 220 need not necessarily be formed on the upper face side of the ceramic layer, and may alternatively be formed at an intermediate position in the thickness direction or on the lower face side. A plurality of recessed portions 220 may also be formed. If a plurality of recessed portions 220 are formed, they may have different shapes.

The gas sensor element 100 of the above embodiment may also have a porous protective layer that covers the front end portion and a region therearound. The porous protective layer is, for example, a ceramic porous body, such as alumina. Having a porous protective layer can prevent moisture in the measurement target gas from entering the inside of the gas sensor element 100 and exerting an unfavorable effect on the gas sensor element 100.

EXAMPLES

Examples of the present invention will be described in detail below. However, the present invention is not limited to these examples.

Experiment 1

Five gas sensor elements were prepared. In each gas sensor element, six ceramic layers were stacked and a heater was formed, as shown in FIG. 1. These gas sensor elements had different configurations of the pair of lead portions, which extended through the first and second substrate layers and connected the electrical resistor of the heating portion to the heater electrode. Except for this, the gas sensor elements had a common configuration. Specifically, the cross-sectional shapes shown in FIGS. 5, 6, 7A, 7B, and 8 were adopted as the cross-sectional shape of the inner wall face of the open-hole portion of the second substrate layer for forming the lead portion, and gas sensor elements according to Examples 1 to 4 and Comparative Example 1 included the lead portions having the respective cross-sectional shapes. In the gas sensor element according to Example 2, the inner wall face of the open-hole portion of the second substrate layer had a cross-sectional shape that is common to that of the gas sensor element according to Example 1. Meanwhile, the gas sensor element according to Example 2 was different from the gas sensor element according to Example 1 in that the inner wall faces of the open-hole portions of the first and second substrate layers were covered with an insulating paste. In the gas sensor element according to Comparative Example 1, the open-hole portion of the second substrate layer was demarcated by a substantially flat inner wall face that does not define a recessed portion and extends substantially parallel in the thickness direction of the second substrate layer. In all of the gas sensor elements according to Examples 1 to 4, the depth of the recessed portion specified by the method according to the above embodiment when the thickness of the second substrate layer was 1 was 0.15.

The rear end side, including the pair of lead portions, of the gas sensor elements according to Examples 1 to 4 and Comparative Example 1 was immersed in water and left as-is for four hours. Thereafter, these gas sensor elements were taken out from water, and moisture on the surface was wiped. A voltage of 12 V was applied to the heating portion via the heater electrode for 30 seconds. It was then checked whether or not delamination had occurred between the second and third substrate layers, including the heating portion and the heater insulating layer that surrounds heating portion. The results were evaluated in the following three levels, namely A to C.

A: No delamination was observed after the voltage was repeatedly applied multiple times under the above conditions.

B: Delamination was observed after the second voltage application.

C: Delamination was observed after the first voltage
application.

Table 1 below shows the results of Experiment 1. As
shown in Table 1, resistance to delamination significantly
improved in Examples 1 to 4 compared to Comparative
Example 1. In addition, it was confirmed from the result of
Example 2 that resistance to delamination also improved
when the material in contact with the inner wall face of the
open-hole portion is other than the conductive paste. The
effectiveness of the invention was confirmed by Experiment
1 above.

TABLE 1

| | Configuration | Result |
|---|---|---|
| Ex. 1 | Recessed portion on upper face side | A |
| Ex. 2 | Recessed portion on upper face side | A |
| Ex. 3 | Recessed portion on lower face side | A |
| Ex. 4 | Two recessed portions on upper and lower face sides | A |
| Comp. Ex. 1 | No recessed portion | C |

Experiment 2

Gas sensor elements in which the depth of the recessed
portion relative to the thickness of the second substrate layer
was changed to 0.05, 0.10, 0.20, and 0.25 from that of the
gas sensor element according to Example 1 were prepared as
gas sensor elements according to Examples 5 to 7 and
Reference Example 1, respectively. These gas sensor ele-
ments were immersed in water under the same conditions as
those of Experiment 1, then moisture on the surface was
wiped, a voltage was applied under the same conditions as
those of Experiment 1, and whether or not delamination had
occurred was checked in the same manner as in Experiment
1. The results were evaluated in the aforementioned three
levels, namely A to C.

Table 2 below shows the results of Experiment 2. As
shown in Table 2, resistance to delamination significantly
improved in Examples 1, 6, and 7. In Example 5, the
delamination resistance was inferior to Examples 1, 6, and
7, possibly because the depth of the recessed portion was
relatively small, but was superior to Comparative Example
1 and Reference Example 1. In Reference Example 1,
delamination occurred. It is conceivable that this is because
the conductive did not sufficiently enter the recessed portion.
The effectiveness of the invention was confirmed by Experi-
ment 2 above.

TABLE 2

| | Recessed portion depth | Result |
|---|---|---|
| Ex. 1 | 0.15 | A |
| Ex. 5 | 0.05 | B |
| Ex. 6 | 0.10 | A |
| Ex. 7 | 0.20 | A |
| Ref. Ex. 1 | 0.25 | C |

LIST OF REFERENCE NUMERALS

100 Sensor element
4 First solid electrolyte layer
6 Second solid electrolyte layer
5 Spacer layer
7 Target gas flow portion (internal space)

11 First diffusion control portion (diffusion control por-
tion)
13 Second diffusion control portion (diffusion control
portion)
30 Third diffusion control portion (diffusion control por-
tion)
16 Fourth diffusion control portion (diffusion control
portion)
20 First internal cavity
40 Second internal cavity (chamber)
17 Third internal cavity
72 Heating portion
73 Lead portion
74 Heater insulating layer
200 Upper face (first face)
201 Lower face (second face)
202 Upper face (first face)
203 Lower face (second face)
210 Upper first internal wall face
211 Lower first internal wall face
212 (Upper) second internal wall face
220 Recessed portion
A1 Center axis
H1 Through-hole
H2 Through-hole
P1 conductive portion

What is claimed is:

1. A gas sensor element comprising:
a heating portion; and
multiple stacked ceramic layers having:
a first face;
a second face on an opposite side to the first face; and
an open-hole portion extending therethrough in a thick-
ness direction from the first face toward the second face
and constituting a through-hole for electrically con-
necting the first face to the second face, wherein,
the multiple stacked ceramic layers are configured to be
heated by the heating portion,
the multiple stacked ceramic layers comprise a first
ceramic layer,
in the first ceramic layer, the open-hole portion is demar-
cated by a first inner wall face extending in the thick-
ness direction, and a second inner wall face continuous
with the first inner wall face and defining a recessed
portion that is recessed inward of the first ceramic layer
relative to the first inner wall face,
the second inner wall face is formed at a position not
continuous with either an upper surface or a lower
surface of the first ceramic layer, and
with the first ceramic layer having a thickness of 1, the
length of the recessed portion to the most distal position
thereof from a position on the first inner wall face that
is closest to a center axis of the open-hole portion is
0.05 or more and 0.20 or less.

2. The gas sensor element according to claim 1,
wherein, with the first ceramic layer having the thickness
of 1, the length of the recessed portion to the most distal
position thereof from the position on the first inner wall
face that is closest to the center axis of the open-hole
portion is 0.10 or more and 0.20 or less.

3. The gas sensor element according to claim 2,
wherein the second inner wall face is continuous over an
entire circumference of the open-hole portion, and the
recessed portion is defined by the second inner wall
face so as to have an annular shape as viewed from the
first face.

4. The gas sensor element according to claim 2, wherein the second inner wall face is present at least either at a position closer to the first face or at a position closer to the second face in the thickness direction.

5. The gas sensor element according to claim 2, wherein a plurality of the second inner wall faces are present along the thickness direction.

6. The gas sensor element according to claim 2, further comprising a conductive portion having conductivity and filling an inside of the open-hole portion.

7. The gas sensor element according to claim 2, wherein the heating portion is arranged on a side of the first face of the first ceramic layer, and the through-hole electrically connects the heating portion to an element on a side of the second face of the first ceramic layer.

8. The gas sensor element according to claim 2, wherein the gas sensor element is configured to measure a concentration of nitrogen oxide in a measurement target gas.

9. The gas sensor element according to claim 1, wherein the second inner wall face is continuous over an entire circumference of the open-hole portion, and the recessed portion is defined by the second inner wall face so as to have an annular shape as viewed from the first face.

10. The gas sensor element according to claim 1, wherein the second inner wall face is present at least either at a position closer to the first face or at a position closer to the second face in the thickness direction.

11. The gas sensor element according to claim 1, wherein a plurality of the second inner wall faces are present along the thickness direction.

12. The gas sensor element according to claim 1, further comprising a conductive portion having conductivity and filling an inside of the open-hole portion.

13. The gas sensor element according to claim 1, wherein the heating portion is arranged on a side of the first face of the first ceramic layer, and the through-hole electrically connects the heating portion to an element on a side of the second face of the first ceramic layer.

14. The gas sensor element according to claim 1, wherein the gas sensor element is configured to measure a concentration of nitrogen oxide in a measurement target gas.

* * * * *